United States Patent [19]
Christy

[11] Patent Number: 5,350,385
[45] Date of Patent: Sep. 27, 1994

[54] SURGICAL STAB WOUND CLOSURE DEVICE AND METHOD

[76] Inventor: William J. Christy, 1324 Sunset Dr., Winter Park, Fla. 32789

[21] Appl. No.: 54,856

[22] Filed: Apr. 28, 1993

[51] Int. Cl.$^5$ .............................................. A61B 17/06
[52] U.S. Cl. .................................... 606/139; 606/146; 606/144
[58] Field of Search ............... 606/139, 144, 145, 146, 606/147

[56] References Cited

U.S. PATENT DOCUMENTS

| | | | |
|---|---|---|---|
| 373,372 | 11/1887 | La Forest King | 606/146 |
| 962,218 | 6/1910 | Heitz-Boyer | 606/146 |
| 2,008,251 | 7/1935 | Hillebrand | 606/146 |
| 2,393,910 | 1/1946 | Karle | 606/146 |
| 3,638,653 | 2/1972 | Berry | 606/146 |
| 3,840,017 | 10/1974 | Violante | 606/146 |
| 4,011,873 | 3/1977 | Hoffmeister | 606/146 |

Primary Examiner—Peter A. Aschenbrenner

[57] ABSTRACT

A device and method are provided for the surgical suturing of narrow incisions that penetrate through a plurality of tissue layers. The device comprises a hollow needle through which suture material is threaded, the needle having the shape of an elongated "J." The method entails inserting the needle into the wound, bringing the tip through one or more layers of tissue, and pulling suture material up through the wound; these steps are repeated for the other side of the wound to form a single stitch, which may then be knotted. In this way one or more subcutaneous layers of tissue may be sutured without involving the skin, which may be sutured using conventional means to complete the closure.

13 Claims, 3 Drawing Sheets

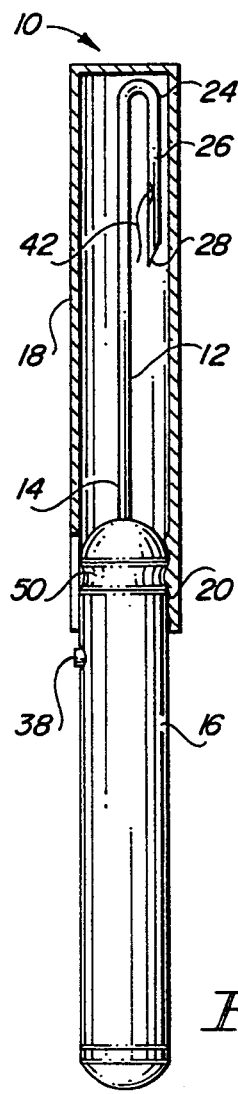
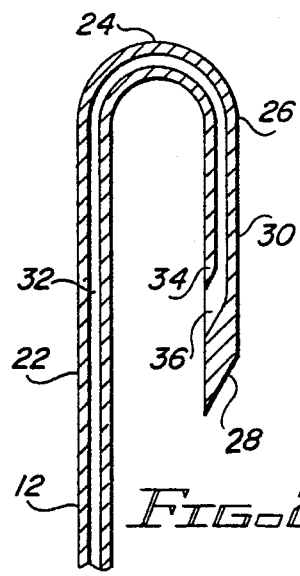
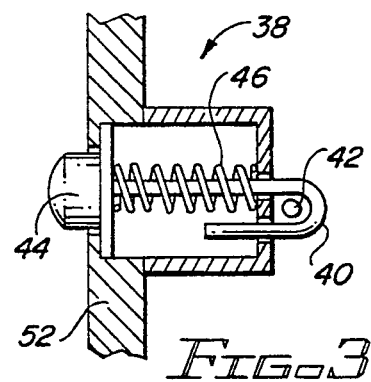
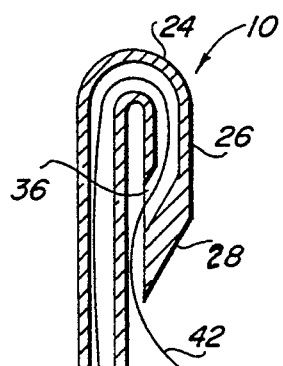
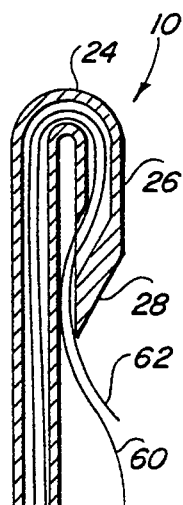
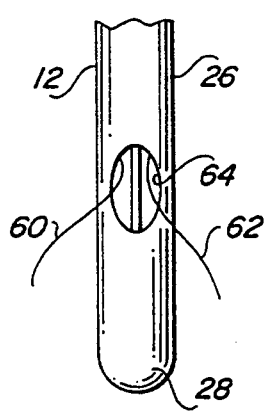
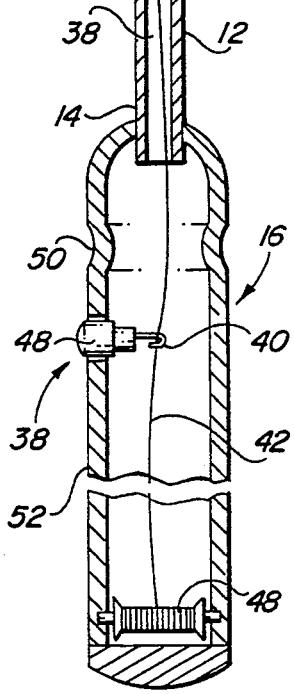
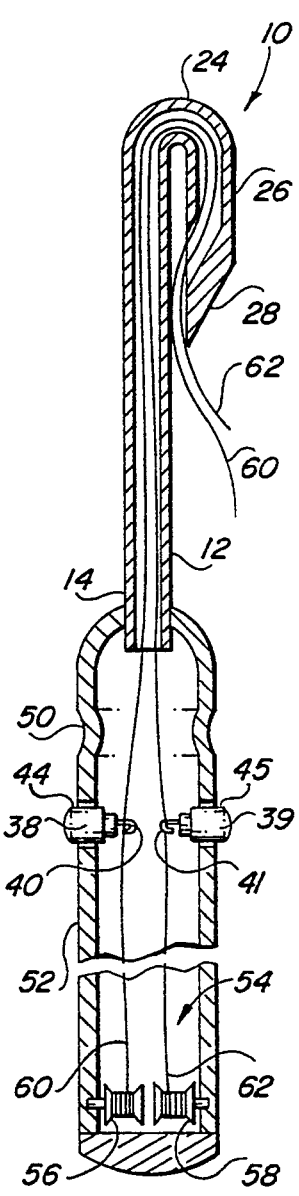

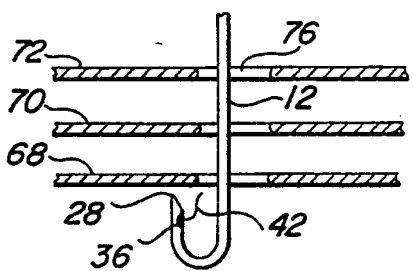
FIG_8(a)
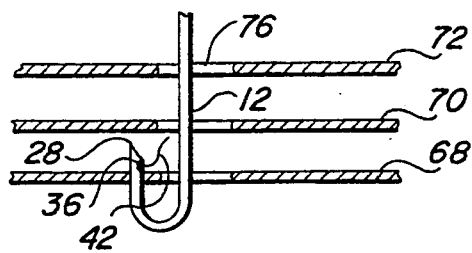
FIG_8(b)
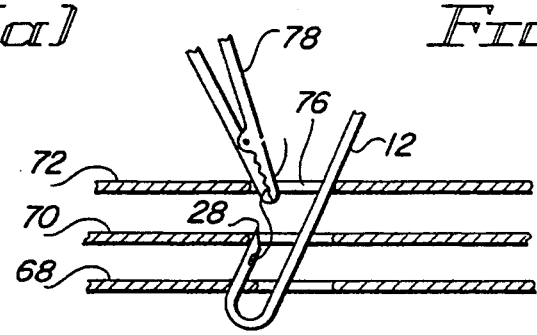
FIG_8(b')
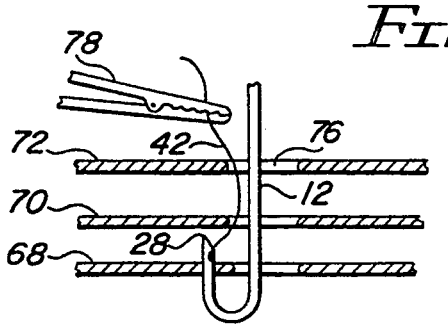
FIG_8(c)
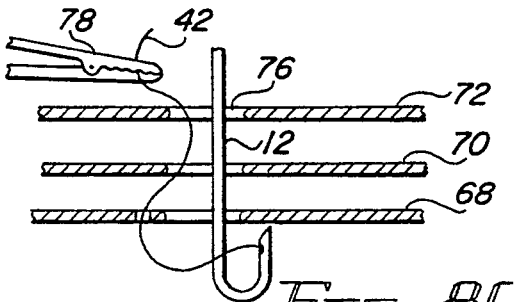
FIG_8(d)
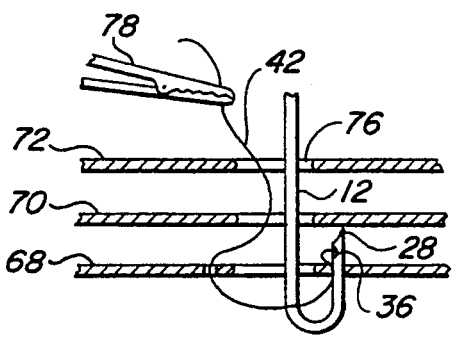
FIG_8(e)
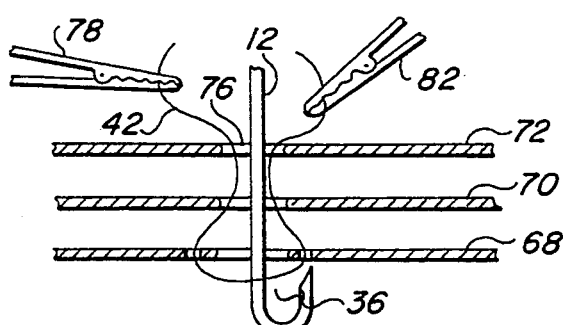
FIG_8(f)
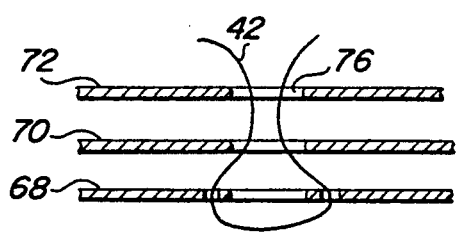
FIG_8(g)
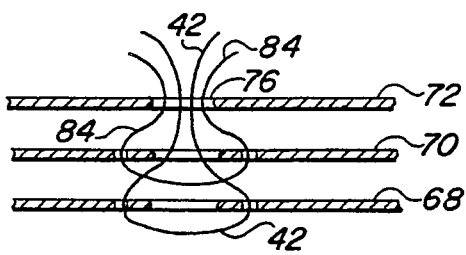
FIG_8(h)

SURGICAL STAB WOUND CLOSURE DEVICE AND METHOD

BACKGROUND OF THE INVENTION

This invention relates generally to the field of surgical devices and, more particularly, to surgical suturing apparati and methods of surgical suturing.

Laparoscopic or endoscopic surgical procedures are now widely used in many specialties in the surgical community. These procedures generally involve a "C"-shaped incision through the navel, through skin, adipose tissue, fascia, muscle, and peritoneum, which comprise the abdominal wall or thoracic wall. Using this method many organs of the gut may be viewed and operated upon: gall bladder, intestines, appendix, uterus, fallopian tubes, ovaries, and lungs.

Trocars, pointed cannulae with pointed obturators for piercing the wall of a cavity, are often used to create ports through which surgical instruments may be passed, instead of making long incisions in the abdominal or thoracic wall. The diameter of the trocar differs based upon the procedure to be performed, and may range from 3 to 33 millimeters.

Multiple trocars may be used so that a variety of instruments may be used simultaneously, such as a camera or magnifying lens, cutting, ligating, grasping, or suturing apparati. In this way, for example, forceps passed through one trocar can grasp tissue while a cutting operation is performed through another, the whole procedure being visualized on a screen connected to a camera inserted into the cavity through a third trocar.

Such microsurgery techniques have made it necessary to perform wound closure on a much smaller scale than was required by the previously used large incisions. Up until now, multiple-layer closure has been utilized, whereby the entire abdominal wall has been sutured together to prevent evisceration or herniation of internal organs through the incision site. Should only the skin tissue be closed, complications can occur that include the viscera pushing up through the tissue. The tissue strangulates an organ that may get pushed up causing infection, peritonitis and possibly death.

Surgical suturing instruments have been the subject of prior references. King (U.S. Pat. No. 373,372, issued Nov. 15, 1887), McBrayer (U.S. Pat. No. 389,235, issued Sep. 11, 1888), and Violante (U.S. Pat. No. 3,840,017, issued Oct. 8, 1974) disclose curved, hollow suture needles with suture thread positioned in and emerging from the bore and having a storage means for suture thread located within or upon a handle into which the suture needle is affixed. Violante's device further comprises a sharpened and beveled tip capable of cutting the suture thread when the procedure is completed. Karle (U.S. Pat. No. 2,327,353, issued Dec. 12, 1940) described a device for surface wound stitching that utilizes two spools of suture thread for creating a lock stitch, not unlike that produced by a conventional sewing machine having a threaded needle that communicates with another spool of thread, the bobbin.

Baber's invention (U.S. Pat. No. 5,152,769, issued Oct. 6, 1992) is specifically directed to a suture needle for laparoscopic procedures. His apparatus is designed for use with a trocar, and comprises a pair of concentric and slidable barrel portions. To the outer barrel is affixed a hollow suture needle having a curved tip and a hole through which suture thread may pass. A hook-shaped member is affixed to the inner barrel. Suturing is then accomplished by rotating the outer barrel to guide the needle through the tissue to be stitched and grasping the suture thread with the hook-shaped member to form a loop, which is held in place within the inner barrel until the next suture is made.

SUMMARY OF THE PRESENT INVENTION

The Surgical Suturing Apparatus

The surgical suturing apparatus of the present invention is directed to closing incisions penetrating a plurality of layers of tissue, particularly narrow incisions such as stab wounds or those formed by trocar punctures.

This device comprises a tubular body, dimensioned to fit into a human hand, in one embodiment having one or more depressions for finger positioning. Suture thread holding means are positioned inside the tubular body, and may consist of a rotatable spool affixed to the interior of the tubular body, upon which suture material is wound. The suture material then is threaded through a means for clamping the suture material to maintain a length of suture material desired. When the suture material is desired to be unclamped, the release means are engaged. The release means extend through the outer surface of the tubular body and communicate with the clamping means. These elements may consist of two opposed hooks that, when in their passive state, define an aperture sufficiently small to clamp the suture material, and a release button positioned on the outer surface of the tubular body that, when pushed, moves one of the hooks laterally sufficiently far to release the suture material.

Onto the tubular body is affixed a hollow suture needle in the shape of a "deep J," comprising an first elongated portion at the proximal end, a curved portion at the distal end, and a second, shorter elongated portion substantially parallel to the first elongated portion, having a pointed tip at its end. These elongated portions may be provided having different dimensions for a variety of surgical procedures. A gate communicating with the bore of the needle is placed along the second elongated portion, away from the pointed tip. Suture material is threaded from the clamping and release means through the bore of the suture needle and emerges out from the gate.

In addition, a sliding retractable sheath mechanism is provided to cover the suture needle portion of the device when not in use, in order to maintain sterility and prevent needle sticks.

Method For Suturing Narrow Incisions

The method for utilizing the above-disclosed apparatus for suturing narrow incisions will now be described.

After unsheathing the needle portion of the device, the needle is inserted into the wound sufficiently deep so that the pointed tip is beneath the deepest layer of tissue to be sutured. Then the tip is brought surfaceward through the first side of the tissue layer until the suture gate, from which suture material is extending, is pulled through, and a suture grasping means, such as a hemostat or forceps, holds the end of the suture material. At this point the suture thread release means are engaged, and the grasping device is used to pull the suture material to the surface of the wound, leaving a length sufficient for tying a knot.

The needle portion of the device is next pushed back into the wound so that the tip is once again beneath the deepest layer of tissue to be sutured, the tip is rotated so that it is beneath the second side of the wound, and the same procedure already described is performed, leaving a second end of suture material outside the surface of the wound, and a knot, usually a double knot, is tied.

This method may be used for multiple layers of tissue, one layer at a time, or it may be used to suture several layers together simultaneously. Following this procedure, conventional surface incision stitching or closing method may be employed to suture the skin.

BRIEF DESCRIPTION OF THE DRAWINGS

A preferred embodiment of the invention along with alternate embodiments are described by way of example with reference to the accompanying drawings in which:

FIG. 1 illustrates the stab wound suturing apparatus in the preferred embodiment including a sheath cover shown in its extended position covering the needle;

FIG. 2 is a partial cross-sectional view of the needle distal end illustrating the needle bore and gate proximate to the tip of the needle;

FIG. 3 is a partial cross-sectional view of the suture release device in the preferred embodiment illustrating the suture material being held by a suture clamp and a spring biasing the clamp against the suture;

FIG. 4 is a partial cross-sectional view of the suturing apparatus illustrating the path of the suture from its spool storage through the release and the needle bore to extend from the needle gate;

FIG. 5 is a cross-sectional view of the apparatus wherein two suture storage spools, on which two sutures are wound; the sutures then are shown threaded through a double release and emerge from a dual channel gate are held;

FIG. 6 is a partial view of the needle distal end illustrating a dual channel gate wherein two sutures are dispensed;

FIG. 8a–8h are illustrations of the three tissue layers useful in disclosing the invention and various needle positions within a stab wound;

DETAILED DESCRIPTION OF PREFERRED EMBODIMENT

Figure 7:
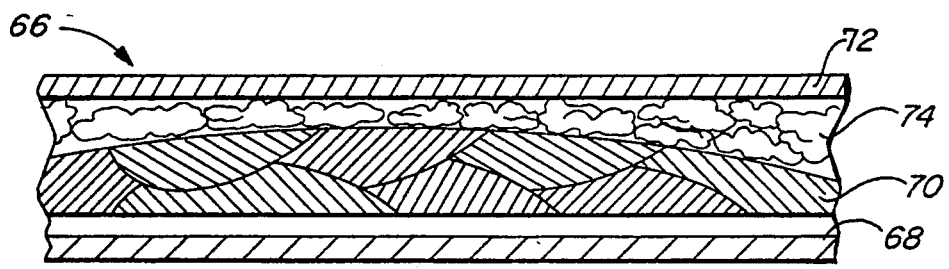
FIG. 7 is a partial cross-sectional view of an abdominal section illustrating by way of example tissue layers from the skin to the abdominal inner wall.

The preferred embodiment of the invention, a surgical suturing apparatus 10, useful in suturing stab wounds or narrow incisions as in the incision created by a trocar used in a laparoscopic of endoscopic surgical procedure will be discussed. As illustrated in FIG. 1, the preferred embodiment of the invention comprises a needle 12 affixed at its proximal end 14 to a tubular body 16. In one embodiment, a sheath cover 18 is slidable over the body 16 and extendible to cover the needle 12 during storage of the suturing apparatus 10. The sheath cover 18 comprises a multiple position sheath holder 20 for locking the sheath into position over the body 16 during use of the apparatus 10.

The needle 12 comprises a first elongated section 22 extending from the proximal end 14 to a curved section 24 and a second straight section 26 extending from the curved section 24 to pointed tip 28 at a distal end 30 of the needle 12 as illustrated in FIG. 1 and further detailed in the partial cross-sectional view of the distal end 30 in FIG. 2. Further reference to FIG. 2 shows a bore 32 which runs from the proximate end 14 of the needle 12 to the distal end 30 where the bore 32 exits the needle wall 34 at a gate 36.

As will be further detailed later in the specification, a suture release 38 is located on the body 16, as illustrated in FIG. 1. FIG. 3 illustrates one embodiment of the suture release 38 used in the preferred embodiment. The release 38 comprises a suture clamp 40 that holds a suture material 42 in a fixed position until pushing a button 44 causes the suture to be released and run free through the suture clamp 40. A spring 46 biases the clamp 40 against the suture material 42 in the holding position.

With reference to FIG. 4, it can be seen that the suture material 42 is stored on a spool 48 rotatably affixed inside the tubular body 16 in the preferred embodiment. The suture 42 is threaded through the suture clamp 40 and into the proximal end 14 of the needle 12 where it continues through the bore 32 and exits the gate 36. FIGS. 4 and 1 also illustrate an arcuate finger recess 50 of the preferred embodiment in the body wall 52 for ease in holding the apparatus 10.

An alternate embodiment of the apparatus 10 comprises the use of dual suture storage 54 using a first spool 56 and a second spool 58 mounted within the body 16 is series or in tandem, as illustrated in FIG. 5. A first 60 and second 62 suture are threaded either through a single release 38 as discussed earlier or a first 38 and a second 39 release having, respectively, a first 40 and a second 41 suture clamp and a first 44 and a second 45 release button and through a bored needle comprising a dual channel gate 64 as illustrated in FIG. 6. It is anticipated that one skilled in the art can devise other embodiments that are combinations of the elements disclosed.

A method for using the preferred embodiment will be disclosed using by way of example the suturing of a small incision associated with a trocar puncture in the abdomen during a laparoscopic surgical procedure. With reference to FIG. 7, it can be seen that the abdominal wall 66 comprises the peritoneum, which will be referred to as the first tissue layer 68, a muscle tissue referred to as a second layer 70 and the skin tissue layer which will be referred to as the third tissue layer 72 for purposes of describing the method of using the suturing apparatus 10. The subcutaneous fat 74 and other wall 66 layers are not needed to demonstrate the use and effectiveness of the preferred embodiment of the invention.

Figure 9:
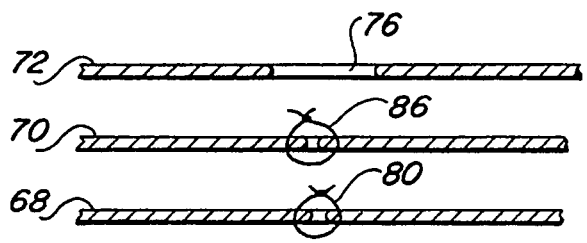
FIG. 9 illustrates the knots tied in the first and second tissue layers after completing the method steps disclosed by the invention.

With reference to the simplified stab wound or narrow incision 76 drawings of FIG. 8, a preferred method for using the apparatus 10 to suture inner tissue layers of the incision 76 will be described by illustrating the various positions of the needle 12 with respect to the three tissue layers of interest in this abdominal wall 66 example. With reference to FIG. 8a, the needle 12 is inserted into the narrow incision 76 sufficiently deep so that the tip 28 of the needle 12 is beneath the deepest layer of tissue 68 to be sutured. In practice, the procedure will require using grasping tissue forceps in order to elevate the innermost lining 68 away from the viscera (not shown) before inserting the needle tip 28 into the innermost layer 68. In this position, a small amount of suture material 42 is extending from the gate 36 and the suture release 38 is in the biased position holding the suture 42 in position. As illustrated in FIG. 8b, the tip 28 is next brought surfacewards through the first layer back towards the opening of narrow incision in order to grab the suture material with a suture grasping means as shown in FIG. 8b'. It is anticipated that this technique will be used during each step of grabbing the suture material even though not explicitly shown in the illustrated drawings. With reference to FIG. 8c, the suture material 42 is grabbed with a suture grasping means 78, the suture release button 44 is pressed, releasing the suture, and the suture is pulled out of the needle 12 and out of the incision 76 sufficient to handle for tying a knot 80, which is the objective of this procedure. While securing the grasping means 78, the needle 12 is pushed into the incision sufficiently to again place the tip 28 below the first tissue layer, the deepest layer 68. The needle is rotated so as to place the tip 28 in a position to be pulled up through another location of the first layer 68, as is illustrated in FIG. 8d. The exact technique can vary, but the suture can be secured at this position so that the suture will more positively be controlled during the subsequent steps. As illustrated in FIG. 8e, the tip 28 is brought surfaceward through the other side of the incision 76 at the first layer 68 sufficient to pull the gate 36 through the first layer 76. Once the suture 42 at the gate 36 is through the first layer 68, the suture is grabbed by a second grasping means 82 and cut near the gate 36, leaving a short length of suture extending sufficient for grabbing. The second grasping means 82 then pulls the suture 42 out of the incision 76 sufficient for tying a knot 80 as illustrated in FIGS. 8f and 9. The needle 12 is then removed from the incision 76 as illustrated in FIG. 8g, and the suture material 42 is ready for tying a knot 80. It is preferred that the steps as described in FIG. 8a through 8g be repeated for the needle 12 penetrating the second tissue layer 70 rather than the first 68 and a suture 84 prepared for tying a knot 86 in the second tissue layer 70, as illustrated in FIG. 8h and shown as knots 80 and 86 in FIG. 9 for the first 68 and second 70 tissue layers, respectively.

Figure 10:
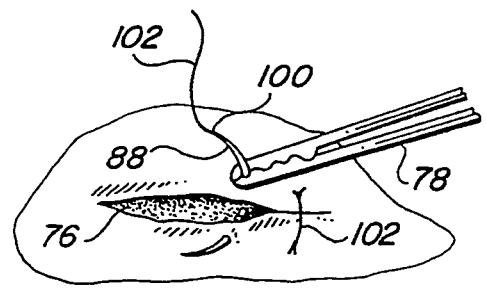
FIG. 10 illustrates a well known suturing of the wound at the skin tissue level.

Once the first 68 and second 70 tissue layers have been sutured as described, the skin or third tissue layer 72 is sutured using a standard needle 88 as illustrated in FIG. 10. The needle 88 illustrated by way of example is of the swage style having a swage eye 100 and suture 102 attached. Various suturing techniques for surface tissue will be selected based on the preference of the surgeon and the surgical procedures appropriate for the specific operation. It is anticipated that some surgeons will suture the skin using the apparatus 10.

Figure 11A:
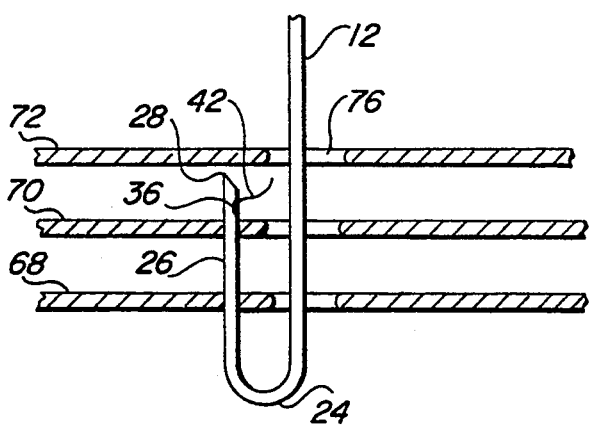
FIG. 11a and 11b illustrates an alternate method of suturing two tissue layers.
Figure 11B:
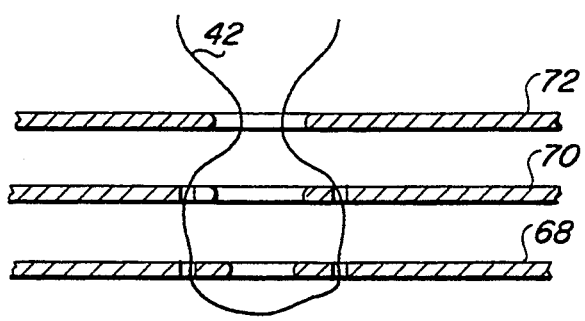

By selecting a needle 12 having a second straight section 26 long enough to penetrate two tissue layers, for example 68 and 70, the above method of suturing can be followed for suturing the two inner layers 68 and 70 as partially illustrated in FIG. 11a and 11b. Second straight sections 26 on varying lengths are provided in the various versions of the preferred embodiment 10 for selection by the surgeon based on the procedure and patient requirements. In addition, by using the dual suture storage 54 and dual channel gate 64 providing a first 60 and second 62 suture, the above procedures can be modified as desired by the surgeon and techniques specific to the needs of the surgeon and procedure developed to meet the specific needs. It is anticipated that one skilled in the art of suturing will devise other steps combining the embodiments and method steps disclosed.

Accordingly, a suturing apparatus is provided which has inherently all those attributes, objects and advantages set forth above, and which provides a new and extremely useful invention of the type and function unique in the light of prior constructions.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiments thereof, and the advantageous new and useful results obtained thereby, the new and useful construct ions, and reasonable mechanical equivalents thereof obvious to those skilled in the art, are set forth in the appended claims.

What is claimed is:

1. A surgical suturing apparatus for closing incisions penetrating a plurality of layers of tissue, comprising:

a tubular body having an inner and an outer surface and a first and second end, and dimensioned to fit into a human hand, the first end having a hole dimensioned to hold suture material;

suture thread holding means positioned inside and attached to the inner surface of the tubular body;

releasable suture thread clamping means positioned inside and attached to the inner surface of the tubular body;

suture thread release means extending through the outer surface of the tubular body and communicating with and operable on the releasable suture thread clamping means; and a suture needle attached to the first end of the tubular body, the suture needle having a bore dimensioned to hold suture material and having a first, proximal end and a second, distal end and with two substantially parallel straight sections each adjacent a corresponding one of the ends and with a curved middle section between the two straight sections, the straight section adjacent the distal end having a pointed tip.

2. The surgical suturing apparatus recited in claim 1, the suture needle further having a suture gate, dimensioned to allow suture material to pass therethrough, positioned along the straight section adjacent the distal end.

3. The surgical suturing apparatus recited in claim 2, further comprising suture material, a proximal end retained on the suture thread holding means, passing through the suture thread clamping means and through the bore in the first end of the tubular body, and proceeding through the bore of the suture needle, the distal end of the suture material extending through the suture gate of the suture needle.

4. The surgical suturing apparatus recited in claim 1, wherein the suture thread holding means comprises a spool around which suture material may be wound, the spool rotatably affixed to the inner surface of tubular body.

5. The surgical suturing apparatus recited in claim 1, wherein the suture thread clamping means comprises a first hook rigidly affixed to the inner surface of the tubular body and a second hook substantially opposed to the first hook and movably affixed to the inner surface of the tubular body, such that when the suture thread release means are not engaged, the first and second hooks form an aperture sufficiently small to clamp suture material, and such that when the suture thread release means are engaged, the second hook is moved laterally toward the first hook to form an aperture sufficiently large to allow suture material to pass through.

6. The surgical suturing apparatus recited in claim 1, further comprising a retractable sheath reversibly positionable over the suture needle.

7. The surgical suturing apparatus recited in claim 1, further comprising:
   a second suture thread holding means, positioned inside and attached to the inner surface of the tubular body;
   a second releasable suture thread clamping means, positioned inside and attached to the inner surface of the tubular body; and
   a second suture thread release means, extending through the outer surface of the tubular body, communicating with and operable on the second releasable suture thread clamping means.

8. The surgical suturing apparatus recited in claim 1, wherein the tubular body has at least one arcuate recess of a size and shape for the reception of the ball of an operator's finger.

9. A method of forming a suture in a subcutaneous layer of a narrow incision that penetrates more than one layer of tissue, comprising the steps of:
   providing a surgical suturing apparatus for closing incisions penetrating a plurality of layers of tissue, comprising:
   a tubular body having an inner and an outer surface and a first and second end, and dimensioned to fit into a human hand, the first end having a hole dimensioned to hold suture material;
   suture thread holding means positioned inside and attached to the inner surface of the tubular body;
   releasable suture thread clamping means positioned inside and attached to the inner surface of the tubular body;
   suture thread release means extending through the outer surface of the tubular body and communicating with and operable on the releasable suture thread clamping means; and
   a suture needle attached to the first end of the tubular body, the suture needle having a bore dimensioned to hold suture material and having a first, proximal end and a second, distal end and with two substantially parallel straight sections each adjacent a corresponding one of the ends and with a curved middle section between the two straight sections, the straight section adjacent the distal end having a pointed tip, the suture needle further having a suture gate dimensioned to allow suture material to pass therethrough, positioned along the straight section adjacent the distal end;
   providing suture material, positioned on the suture thread holding means and clamped by releasable suture thread clamping means, threading the suture material through the needle bore, the suture material extending out from the suture needle gate;
   providing suture material grasping means;
   inserting the suture needle into the incision sufficiently deep that the pointed tip of the suture needle is beneath the deepest layer of tissue to be sutured;
   bringing the suture needle pointed tip surfaceward through a first side of the incision sufficiently far to pull the suture material through a first side of the deepest layer of tissue to be sutured, penetrating only one layer of tissue;
   grasping the suture material that has been pulled through the tissue layer with the grasping means;
   engaging the suture thread release means;
   pulling the suture material out of the incision with the use of the grasping means to a length sufficient for tying a knot;
   pushing the suture needle into the incision sufficiently deep that the pointed tip is again beneath the deepest layer of tissue to be sutured;
   rotating the suture needle;
   bringing the suture needle pointed tip surfaceward through a second side of the incision sufficiently far to pull the suture material through the deepest layer of tissue to be sutured, penetrating only one layer of tissue;
   grasping the suture material that has been pulled through the tissue layers with the grasping means;
   pulling the suture material out of the incision with the use of the grasping means to a length sufficient for tying a knot;
   disengaging the suture thread release means;
   cutting the suture material; and
   tying a knot.

10. The method of forming a suture in a subcutaneous layer of a narrow incision recited in claim 9, wherein tying a knot comprises tying a double knot.

11. A method of forming a suture in a subcutaneous layer of a narrow incision that penetrates more than one layer of tissue, comprising the steps of:
   providing a surgical suturing apparatus for closing incisions penetrating a plurality of layers of tissue, comprising:
   a tubular body having an inner and an outer surface and a first and second end, and dimensioned to fit into a human hand, the first end having a hole dimensioned to hold suture material;
   suture thread holding means positioned inside and attached to the inner surface of the tubular body;
   releasable suture thread clamping means positioned inside and attached to the inner surface of the tubular body;
   suture thread release means extending through the outer surface of the tubular body and communicating with and operable on the releasable suture thread clamping means; and
   a suture needle attached to the first end of the tubular body, the suture needle having a bore dimensioned to hold suture material and having a first, proximal end and a second, distal end and with two substantially parallel straight sections each adjacent a corresponding one of the ends and with a curved middle section between the two straight sections, the straight section adjacent the distal end having a pointed tip, the suture needle further having a suture gate dimensioned to allow suture material to pass therethrough, positioned along the straight section adjacent the distal end;
   providing suture material, positioned on the suture thread holding means and clamped by releasable suture thread clamping means, threading the suture material through the needle bore, the suture material extending out from the suture needle gate;

providing suture material grasping means;

inserting the suture needle into the incision sufficiently deep that the pointed tip of the suture needle is beneath the deepest layer of tissue to be sutured;

bringing the suture needle's pointed tip surfaceward through a first side of the incision sufficiently far to pull the suture material through a plurality of tissue layers;

grasping the suture material that has been pulled through the tissue layers with the grasping means;

engaging the suture thread release means;

pulling the suture material out of the incision with the use of the grasping means to a length sufficient for tying a knot;

pushing the suture needle into the incision sufficiently deep that the pointed tip is again beneath the deepest layer of tissue to be sutured;

rotating the suture needle;

bringing the suture needle's pointed tip surfaceward through a second side of the incision sufficiently far to pull the suture material through the plurality of tissue layers to be sutured;

grasping the suture material that has been pulled through the tissue layers with the grasping means;

pulling the suture material out of the incision with the use of the grasping means to a length sufficient for tying a knot;

disengaging the suture thread release means;

cutting the suture material; and tying a knot.

12. The method of forming a suture in a subcutaneous layer of a narrow incision recited in claim 11, wherein tying a knot comprises tying a double knot.

13. A method of forming a suture in a narrow incision that penetrates more than one layer of tissue, comprising the steps of:

providing a surgical suturing apparatus for closing incisions penetrating a plurality of layers of tissue, comprising:

a tubular body having an inner and an outer surface and a first and second end, and dimensioned to fit into a human hand, the first end having a hole dimensioned to hold suture material;

suture thread holding means positioned inside and attached to the inner surface of the tubular body;

releasable suture thread clamping means positioned inside and attached to the inner surface of the tubular body;

suture thread release means extending through the outer surface of the tubular body and communicating with and operable on the releasable suture thread clamping means; and a suture needle attached to the first end of the tubular body, the suture needle having a bore dimensioned to hold suture material and having a first, proximal end and a second, distal end and with two substantially parallel straight sections each adjacent a corresponding one of the ends and with a curved middle section between the two straight sections, the straight section adjacent the distal end having a pointed tip, the suture needle further having a suture gate dimensioned to allow suture material to pass therethrough, positioned along the straight section adjacent the distal end;

providing suture material, positioned on the suture thread holding means and clamped by releasable suture thread clamping means, threading the suture material through the needle bore, the suture material extending out from the suture needle gate;

providing suture material grasping means;

inserting the suture needle into the incision sufficiently deep that the pointed tip of the suture needle is beneath the deepest layer of tissue to be sutured;

bringing the suture needle pointed tip surfaceward through a first side of the incision sufficiently far to pull the suture material through a plurality of tissue layers to be sutured, without penetrating the skin layer;

grasping the suture material that has been pulled through the tissue layer with the grasping means;

engaging the suture thread release means;

pulling the suture material out of the incision with the use of the grasping means to a length sufficient for tying a knot;

pushing the suture needle into the incision sufficiently deep that the pointed tip is again beneath the deepest layer of tissue to be sutured;

rotating the suture needle;

bringing the suture needle pointed tip surfaceward through a second side of the incision sufficiently far to pull the suture material through a plurality of tissue layers to be sutured, without penetrating the skin layer;

grasping the suture material that has been pulled through the tissue layer with the grasping means;

pulling the suture material out of the incision with the use of the grasping means to a length sufficient for tying a knot;

disengaging the suture thread release means;

cutting the suture material;

tying a knot; and closing the incision in the skin tissue layer.

* * * * *